(12) United States Patent
Craighead et al.

(10) Patent No.: US 7,316,769 B2
(45) Date of Patent: Jan. 8, 2008

(54) LENGTH-DEPENDENT RECOIL SEPARATION OF LONG MOLECULES

(75) Inventors: Harold G. Craighead, Ithaca, NY (US); Stephen W. Turner, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 541 days.

(21) Appl. No.: 10/102,268

(22) Filed: Mar. 19, 2002

(65) Prior Publication Data

US 2002/0160356 A1 Oct. 31, 2002

Related U.S. Application Data

(60) Provisional application No. 60/277,136, filed on Mar. 19, 2001.

(51) Int. Cl.
*G01N 27/26* (2006.01)
*B01D 59/42* (2006.01)
*C12N 13/00* (2006.01)

(52) U.S. Cl. .................. 204/450; 435/173.1
(58) Field of Classification Search ............. 435/173.1; 204/450
See application file for complete search history.

(56) References Cited

U.S. PATENT DOCUMENTS

| | | | |
|---|---|---|---|
| 5,135,627 A | 8/1992 | Soane | 204/182.8 |
| 5,340,452 A | 8/1994 | Brenner et al. | 204/180 |
| 5,427,663 A | 6/1995 | Austin et al. | 204/180.1 |
| 5,599,432 A | 2/1997 | Manz et al. | 204/451 |
| 5,650,055 A * | 7/1997 | Margolis | 204/518 |
| 5,651,900 A | 7/1997 | Keller et al. | 216/56 |
| 5,707,799 A | 1/1998 | Hansmann et al. | 435/6 |
| 5,800,690 A | 9/1998 | Chow et al. | 204/451 |
| 5,837,115 A | 11/1998 | Austin et al. | 204/450 |
| 5,842,787 A | 12/1998 | Kopf-Sill et al. | 366/340 |
| 5,882,465 A | 3/1999 | McReynolds | 156/285 |
| 5,904,824 A | 5/1999 | Oh | 204/601 |
| 5,938,923 A | 8/1999 | Tu et al. | 210/490 |
| 5,948,227 A | 9/1999 | Dubrow | 204/455 |
| 5,958,694 A | 9/1999 | Nikiforov | 435/6 |
| 6,042,710 A | 3/2000 | Dubrow | 204/454 |
| 6,043,080 A | 3/2000 | Lipshutz et al. | 435/287.2 |
| 6,093,296 A | 7/2000 | Soane et al. | 204/451 |
| 6,110,339 A | 8/2000 | Yager et al. | 204/451 |
| 6,132,578 A | 10/2000 | Kambara et al. | 204/451 |
| 6,156,273 A | 12/2000 | Regnier et al. | 422/70 |
| 6,186,660 B1 | 2/2001 | Kopf-Sill et al. | 366/340 |
| 6,193,866 B1 | 2/2001 | Bader et al. | 204/450 |
| 6,414,043 B1 * | 7/2002 | Asher et al. | 521/61 |
| 6,454,789 B1 | 9/2002 | Chen et al. | 607/88 |
| 6,635,163 B1 * | 10/2003 | Han et al. | 204/450 |
| 6,685,810 B2 * | 2/2004 | Noca et al. | 204/450 |

OTHER PUBLICATIONS

Han et al. "Entropic trapping and sieving of long DNA molecules in a nanofluidic channel" J. Vac. Sci. Technol. A 17(4): 2142-2147, Jul., Aug. 1999.*
Webster's II New Riverside Dictionary (1994) (Houghton-Mifflin: Boston, MA) p. 740.*
Viovy, J-L. "Electrophoresis of DNA and other Polyelectrolytes: Physical Mechanisms" Reviews of Modern Physics (Jul. 2000) 72(3): 813-872.*
Long et al. "Separation of polyelectrolytes by porous membranes permeation" C. R. Acad. Sci. Paris. vol. 321, Series IIb, p. 239-246 (1995).*
Deutsch et al. "Macromolecular separation through a porous surface" J. Chem. Phys. 106(22): 9376-9381 (Jun. 8, 1997).*
Chou, C. , et al., "Sorting by Diffusion: An Asymmetric Obstacle Course for Continuous Molecular Separation", *PNAS*, 96 (24), (Nov. 23, 1999), pp. 13762-13765.
Nixon, G. I., et al., "Entropic Trapping and electrophoretic drift of a polyelectrolyte down a channel with a periodically oscillating width", *Physical Review E*, 53 (5), (May 1996), pp. 4969-4980.
Volkmuth, W. D., et al., "DNA electrophoresis in microlithographic arrays", *Nature*, 358, (Aug. 13, 1992), pp. 600-602.
Volkmuth, W. D., et al., "Trapping of branched DNA in microfabricated structures", *PNAS*, 92 (15), (Jul. 1995), pp. 6887-6891.

* cited by examiner

*Primary Examiner*—Sandra E. Saucier
*Assistant Examiner*—Susan Hanley
(74) *Attorney, Agent, or Firm*—Wilson Sonsini Goodrich & Rosati (57) ABSTRACT

Separation of long molecules by length is obtained by forcing such molecules to traverse a boundary between a low free-energy region and a high free-energy region. In one embodiment, the high free-energy region is a dense pillar region or other structure formed on a semiconductor substrate. One or more membranes are used in further embodiments. The low free-energy region is a larger chamber formed adjacent the high free-energy region. A recoil phase allows longer molecules not fully driven into the high free-energy region to recoil into the low free-energy region. In a further variation, the high free-energy region is a membrane having nanoscale holes.

18 Claims, 5 Drawing Sheets

LENGTH-DEPENDENT RECOIL SEPARATION OF LONG MOLECULES

This application claims the benefit under 35 U.S.C. § 119(e) of priority to U.S. Provisional Patent Application Ser. No. 60/277,136, filed Mar. 19, 2001, which is incorporated herein by reference.

FIELD OF THE INVENTION

The present invention relates to separation of long molecules, and in particular to Length-Dependent recoil separation of long molecules.

BACKGROUND OF THE INVENTION

In its native environment, the structure of DNA is strongly influenced by the presence of cellular components such as histones, which bind the DNA helping to stabilize it and assist with its organization during cell division. The familiar shape of chromosomes is due primarily to a complex condensation process caused by interactions between DNA and these nuclear proteins which bind to it.

Stripped of all of these other materials, DNA behaves quite differently. The conformation and motion of DNA by itself in solution are dominated by constant thermal bombardment and statistical effects. On the nanometer scale, DNA is a stiff molecule. The stiffness of the molecule is described by a parameter called the persistence length. Despite the relative stiffness of DNA, for sufficiently long molecules it tends to form a spherical "blob", which is the technical term used by the polymer dynamics community to refer to the conformation of a polymer in free solution. The size of this blob depends on the length of the DNA molecule and the persistence length. DNA is a highly charged molecule, and because the normal aqueous buffer solutions used with DNA have high densities of free ions, the electrostatic forces on DNA molecules are strongly influenced by the screening effects of charges called counterions which are attracted to the DNA molecule. Because the DNA molecules are charged, they move under the influence of an electric field, but the details of this motion are complicated by hydrodynamic interactions between molecules and their counterions. It turns out that the mobility (the ratio of the drift velocity to the applied field) does not depend on the size of the molecule. This is the reason gels are used for separating DNA—the interactions between the DNA and the polymer chains in the gel are responsible for the mobility differences between different sized molecules. Gels fail, however, when the DNA chains get very long. The field-induced elongation of the molecule in the axial direction spoils the length dependence of the mobility and for long chains there is no separation.

It is possible to extend the operational range of gel electrophoresis by reducing the field, but the time required for a separation quickly grows to unreasonable durations. A host of strategies for avoiding this limit have been developed, but still the separation of long DNA strands by gel electrophoresis is a time-consuming process.

There is a need for a separation technique that does not exhibit adverse length dependence. There is a further need for a long molecule separation technique that can be done in a short time.

SUMMARY OF THE INVENTION

Separation of long molecules by length is obtained by forcing such molecules to traverse a boundary between a low free-energy region and a high free-energy region. The boundary between these two regions creates a "free-enegry barrier" which impedes the passage of molecules in the direction from low free-energy to high free-energy. In one embodiment, the high free-energy region is a dense pillar region which induces a reduction in entropy of the molecules. The structure is formed on a semiconductor substrate. The low free-energy region is a larger chamber or structure formed adjacent the high free-energy region.

In one embodiment, the low free-energy region comprises a chamber, and the high free-energy region comprises a region of dense pillars. The low free-energy region corresponds to a high entropic region, and the high free-energy region corresponds to a low entropic region, because of the relationship between entropy and free energy F=U−TS. The low and high free-energy regions are created by opposing electric fields with a discrete boundary in a further embodiment. Other types of structures also provide a sufficient entropic barrier, such as fritglass pate and mesopourous materials. The barrier is two-dimensional for applications such as a semiconductor chip products and three dimensional for further applications.

In one embodiment the high free-energy region comprises nanoscale holes in a membrane. Such membranes are commercially available and are manufactured by techniques such as the track-etch technique known in the art of membrane filter manufacture. In this technique, a polycarbonate membrane is subjected to bombardment by high-energy ionic nuclear fragments. These fragments cause chemical changes to the polymer matrix in the vicinity of the path along which the ion travels. These chemical changes change the solubility of the matrix in some etchants, such as potassium hydroxide, allowing the tracks to be developed into small holes. These holes can be made very regular in size and shape, and can range in size from 10 nm in diameter or smaller up to several microns. In the present embodiment, the membrane is contacted with the medium in which the molecules are suspended and the force on the molecules is directed perpendicular to the membrane. The free-energy barrier is formed by the lower entropy of molecules situated inside the pores in the membrane. A further embodiment is several of these membranes stacked together to form an array of juxtaposed barriers in which separation occurs. An open fabric of fine threads or a surface texture modification of the membrane itself restricts contact between adjacent membranes to those areas elevated by the texturing.

If one applies a force directed to push a molecule towards a region of high free-energy, there will exist a critical force below which there will be insufficient impetus to drive molecules into this high free-energy region. Above the critical force the molecules will be readily driven into the high free-energy region. It should be noted that the transition is not abrupt, as thermal fluctuations can occasionally cause molecules to make the transition even when the force is subcritical.

In an embodiment of the invention, a subcritical force is applied to push molecules upstream from the high entropic region to a boundary between the high and low entropic regions, where they will stop for lack of sufficient force. A pulse of supercritical force is applied for a duration. During this pulse, molecules undergo a period of transition from the low free-energy region into the high free-energy region. For a particular duration, some molecules will be short enough to be promoted entirely into the high free-energy region, while some molecules will be sufficiently long that they will fail to be completely promoted into the high free-energy region, and some portion of these longer molecule will remain in the low free-energy region at the end of the pulse. The duration and voltage level of the pulse can be selected dependent on the length of molecule desired to be separated. In one embodiment of the invention, the motive force is an electric field. Other forces may also be used such as pressure, gravity and centrifugal forces.

When the pulse is complete, most molecules that are not completely within the high free-energy region extract themselves back into the low free-energy in a recoil phase, while most molecules with no portion left in the low free-energy region remain in the high free-energy region. When the recoil phase is complete, the molecules remaining in the high free-energy region are generally of shorter length. Thus molecular separation is effected. In a further embodiment, a retrograde pulse is provided to enhance extraction.

The process is repeated in one embodiment with progressively longer and longer pulses to observe and separate a broad range of lengths. In a further embodiment, repetitive pulses of the same length are serially staged to amplify selectivity in a narrower range of lengths.

In further embodiments, a lateral or longitudinal AC voltage is applied during the recoil phase to speed the extraction of longer molecules. Further reducing the entropy of the low entropy region is done to further speed the extraction or recoil of longer molecules. The temperature of the system may also be increased with a similar effect of increasing the energy difference between the two regions.

DETAILED DESCRIPTION OF THE INVENTION

In the following description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the scope of the present invention. Values for parameters described may be further modified, but may not function as well as the values provided in the description. The following description is, therefore, not to be taken in a limited sense, and the scope of the present invention is defined by the appended claims.

Figure 1:
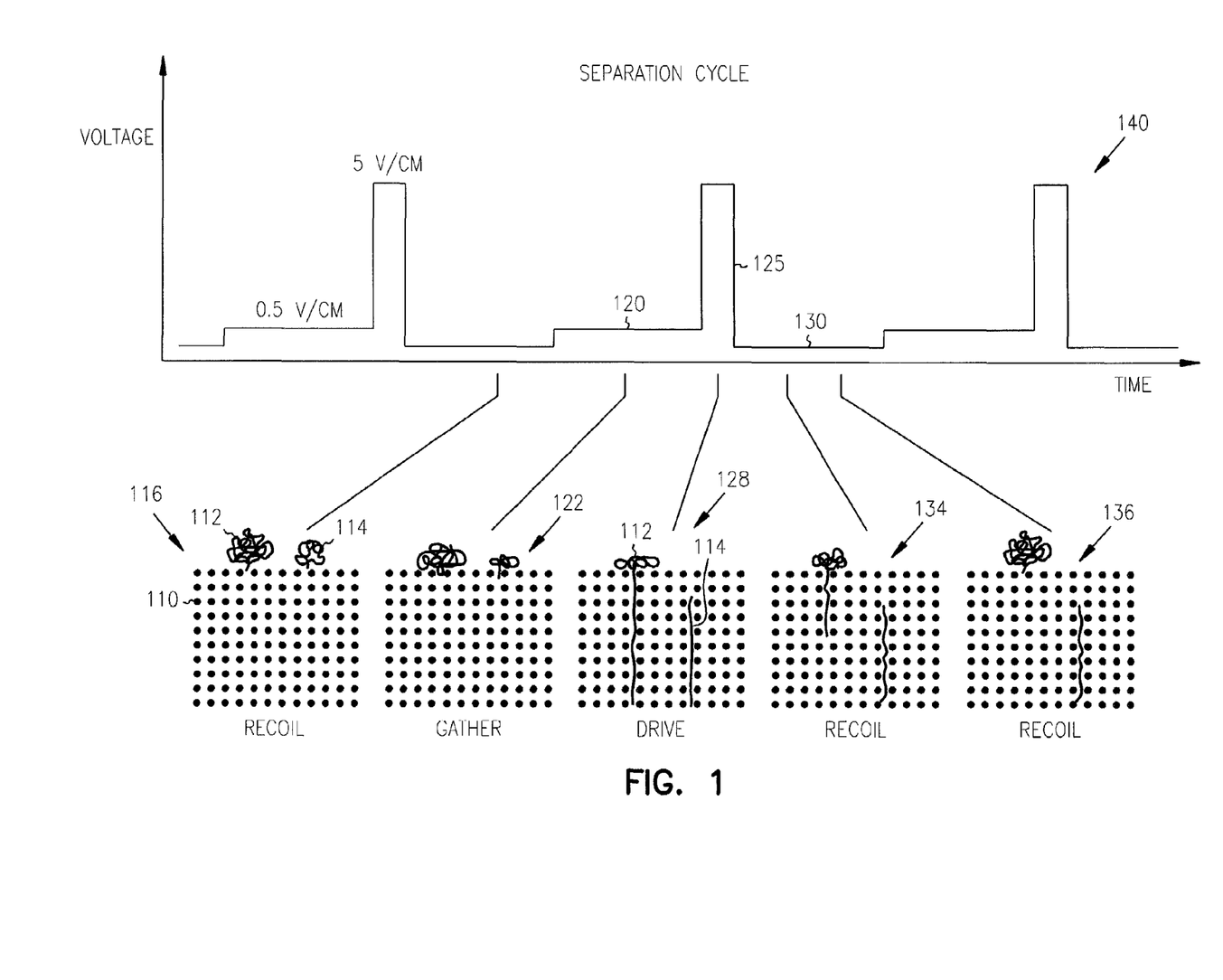
FIG. 1 is a timeline graphic representation of a molecule separation process utilizing a force barrier.

A separation cycle using a free-energy barrier, and pulses of force is represented in FIG. 1. In this embodiment, the energy barrier comprises a region of dense pillars or a porous membrane 110 that provides an area of high free-energy. Two molecules, a long molecule 112 and a shorter molecule 114 are shown on a low free-energy side of the free-energy barrier. The pillar region 110 is shown at a number of different times corresponding to different phases in a program of various applied force levels. At a first time, 116, minimal if any force is applied across the pillar region. The molecules 112 and 114 are located on the low free-energy side of the force barrier. At a second time, 122, the molecules are represented in the same portions of the pillar region 110, but a gathering force 120 is provided across the pillar region causing the molecules to gather at the force barrier. A higher force pulse 125 is applied at 128, causing the long molecule to become partially driven into the dense pillar region. A portion of the long molecule 112 still remains outside the pillar region at the conclusion of the pulse 125. The shorter molecule 114 has been driven fully into the dense pillar region.

At the conclusion of the higher force pulse 125, the force drops back down to its initial level identified at 130 at time 134. During this lower force level, the longer molecule recoils back to the area lower free-energy, completing its recoil at time 136. The process may be repeated one or more times as indicated at 140.

The gather stage at 122 utilizes a subcritical force to push the molecules, such as DNA molecules upstream from the dense pillar region against the boundary, where they are stopped because the field is insufficient to overcome the free-energy barrier.

The drive pulse 125 is a short pulse of high force strength (supercritical force), well over the critical value to start driving the molecules into the dense pillar region. In this embodiment the obstacles cause the molecules reptate into the array of dense pillars. After a time, some of the molecules 114 have completely entered the dense pillar region, while others 112 have some portion still in the low free-energy region.

The recoil time is a time when the molecules are actually separated according to size. If a molecule is not completely in the dense pillar region, it extracts itself due to the forces induced by the difference in free-energy between the two regions. Molecules which have no part left in the low free-energy region remain stationary following the short high field pulse. In one embodiment, the process is repeated iteratively with progressively longer and longer pulse durations suitable for a broad range of molecule lengths. It can also be repeated with the same conditions to maximize the sensitivity in a smaller range of molecule length. The barriers can be serially staged to amplify the selectivity.

Forces are felt by a molecule whenever it traverses the boundary between regions of high free-energy and low free-energy. It causes the molecule to recoil from the region of high free-energy to the region of low free-energy. During the recoil phase of the motion, there are no applied fields in an embodiment of the invention. Thus, the only force acting to impede the recoil motion is the viscous drag between the molecule and the walls of the device. Longer molecules require more time to recoil from the dense pillar region. The recoil time increases like the square of the length because longer molecules have greater friction and they have farther to go. In one embodiment, pore size (the distance between pillars or the size of pores in a membrane) is decreased to further reduce the entropy in the confined region and increase the rate of recoil. In another embodiment the distance between the floor and ceiling of the chamber is made smaller in the high-free energy region to further reduce the entropy of molecules in the confined region and increase the rate of recoil.

When a DNA molecule is trapped at an abrupt entropic barrier, the radius of gyration is much smaller than the length of the onset of the barrier, so it is not appropriate to treat the molecule as a point particle, with a potential modified by the entropy. Where the onset of the barrier is abrupt, it is necessary to consider the details of the conformation of a molecule as it traverses the boundary.

Consider the case of a DNA strand in a tube with an abrupt constriction. Suppose the molecule is being driven by an electric field. When the molecule reaches the constriction, it must surmount the free energetic barrier presented by the change in entropy between the wide region and the thin region.

For sufficiently long molecules the entropy is approximately an extensive quantity. That is to say, if a molecule of length, 1, in a particular region has an entropy S, then a molecule of length 2*1 will have an entropy of approximately 2*S. Moreover, for a molecule part occupying the thick region and part occupying the thin region, the entropy will be approximately a weighted sum of the characteristic entropies of each region.

The most expedient method for generating a value for the entropic force is a Monte Carlo simulation. It turns out that the values for the absolute entropy for a molecule in either region are not required, just the difference in entropy between the two.

Figure 2:
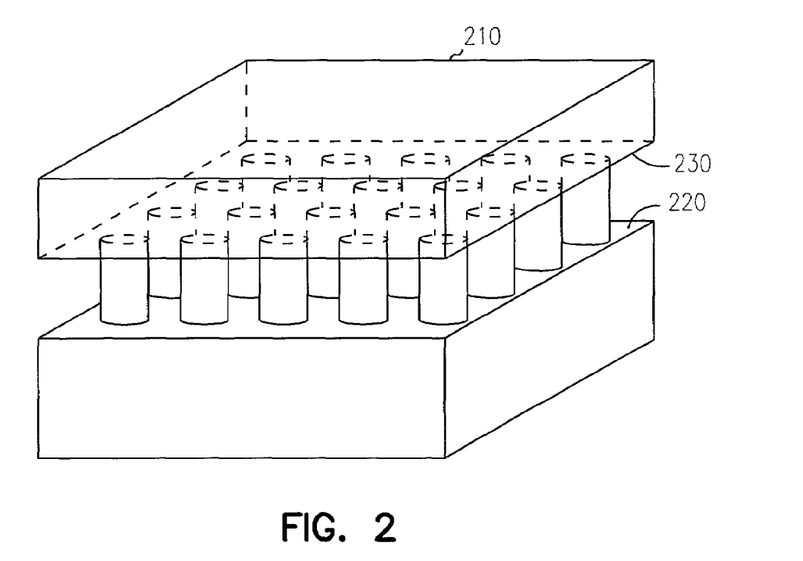
FIG. 2 is a block diagram representation of obstacles used to create the force barrier of FIG. 1.

A two dimensional planar array of obstacles/pillars is shown in FIG. 2 generally at 210. In one embodiment, the persistence length of the polymer is about 65 nm. The distance between a floor 220 and a ceiling 230 of the dense pillar region is about 80 nm. In this case, it is expedient to treat the contour of the molecule as two-dimensional. This is done because the floor-to-ceiling height is on the same order as the persistence length. For stiff polymers like DNA, self-avoidance can be ignored because self-interactions are rare. For DNA this is an acceptable approximation, because the persistence length is more than 30 times larger than the diameter of the molecule. In one embodiment the high free-energy region in FIG. 2 comprises nanoscale holes in a membrane as described further below.

Figure 3:
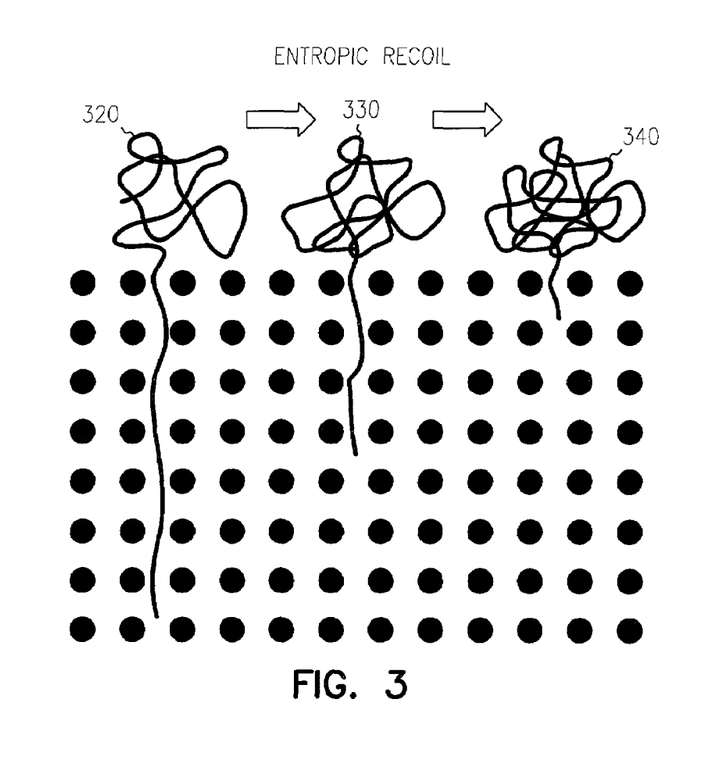
FIG. 3 is a graphic representation of entropic recoil over time.

A dense pillar region is shown at 310 in FIG. 3. A molecule is shown partially driven into the dense pillar region at 320 following application of a pulse of force. At 330, the molecule is shown partially recoiled from the dense pillar region, and at 340, the molecule is shown just about fully recoiled after a lapse of time. The time it takes to recoil is dependent on the length of the molecule. Reducing the recoil time can be done by applying a lateral alternating current field calculated to make the molecule move sideways with respect to the pillars a distance approximately equal to the pillar separation. However, the AC field may be applied to cause the molecule to more further or shorter distances. In one embodiment, the AC field is approximately 100 hertz, designed to make the molecule move at a speed of approximately 10 micrometers per second. A longitudinal AC field may also be applied in a similar manner.

In one embodiment, the gathering field is ¼ to ½ volts per centimeter to drive the molecules to the boundary. The drive pulse is approximately five volts per centimeter in one embodiment for DNA molecules, but is highly dependent on the pillar spacing. The pillar spacing for DNA molecules was 40 to 70 nanometers in one embodiment, but also may be much larger with smaller effect. A pillar spacing of ½ micron or more also provides some effect for DNA molecules. If the drive pulse is too low, the minimum force to cross the barrier will not be obtained, and there will be no separation of the molecules. If the drive pulse is too high, it may cause initiation of hernias along the molecule, causing the longer molecules to also be completely driven across the barrier.

In further embodiments, the pulse of applied force is provided by pressure, gravity, centrifugal force, or some other force that causes molecules to move. The force barrier in further embodiments comprises fritglass plate or mesopourous materials. A fritglass plate comprises nanoparticles fused together to form a glassy sandstone type material. A mesopourous material comprises naturally occurring zeolytes and manmade nanostructures having random nanostructure pores. In yet a further embodiment, an electrical energy barrier is used. The electrical enegry is uniform on both sides to form a tightly defined boundary.

The use of a force barrier in combination with pulses of force followed by a recoil phase may also be used on other biologicals, including proteins. In the case of proteins, the pillar spacing and drive pulse are modified consistent with the persistent length of the desired molecule. It is also used for washing and separation and rinsing in further embodiments without allowing the desired molecule to escape. It should be noted that these are just alternative forms of separating molecules and portions of molecules.

In a further embodiment, multiple spaced free-energy barriers are formed. When cycled with alternating drive pulses and recoil phases, a molecule length resolution is obtained that resembles pulse field gel electrophoresis, but performs better. In one embodiment, the number of barriers is approximately 100.

Figure 4:
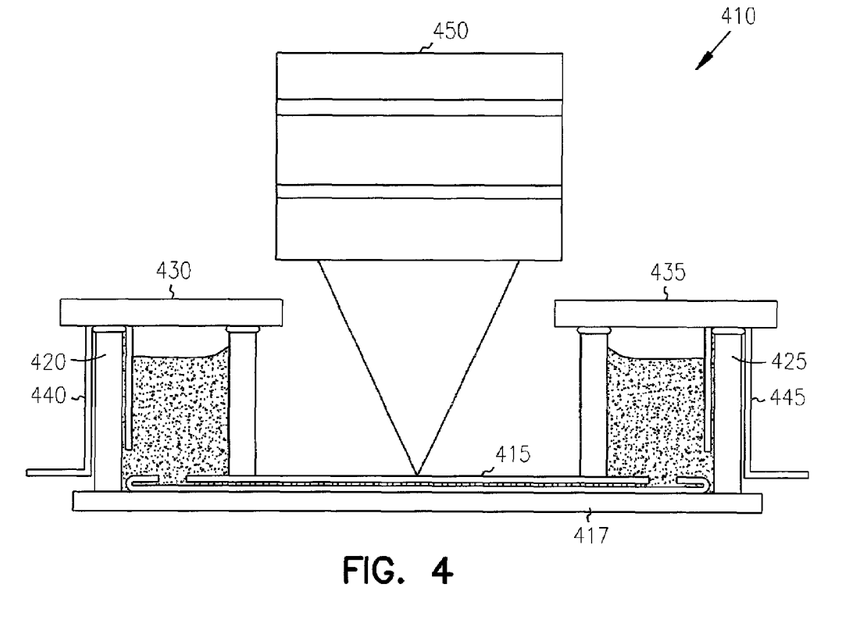
FIG. 4 is a block representation of an apparatus for performing the process of FIG. 1.

FIG. 4 is a block representation of an apparatus 410 for separating molecules by use of a free-energy barrier. The free-energy barrier is represented at 415 as a dense pillar region supported on a structure 417, which is glass in one embodiment or other supporting material that is electrically isolated from the force barrier 415. A pair of reservoirs for molecules in a buffer solution are represented at 420 and 425, with corresponding covers 430, 435. The covers are made of glass in one embodiment to prevent evaporation. Each reservoir contains an electrode 440 and 445 that is in contact with the buffer solution to provide an electric field between the two reservoirs 420 and 425. The buffer solution is an electrolytic solution in one embodiment, and extends throughout the pillars of the force barrier 415. A device for viewing molecules from a distance is indicated at 450. Device 450 comprises a fluorescence microscope in one embodiment, which allows the direct visualization of individual DNA molecules as they interact with the boundary between the dense pillar region and the free region.

The DNA samples for one embodiment are extracted from phages, primarily T2 and T7 phage DNA. The T2 DNA is more than four times as long as the T7 with lengths of 164 and 37.9 kbp, respectively. This translates to a fully stretched length of 50.8 um and 11.7 um, respectively. One of the standard buffer solutions for working with DNA is a mixture of 89 mM Tris-borate and 2 mM EDTA which is abbreviated TBE. The solution is usually shipped ten times concentrated, a form frequently called "10×TBE". In one embodiment of the invention, a solution at 5 times higher concentration than usual, referred to as 5×TBE. The higher salt concentration helps suppress electro-endoosmosis which is sometimes called electro-osmosis or electrokinetic flow, in which an electric field applied across a fluid-filled capillary causes flow in the capillary. It is caused by donation of charges from the capillary wall to the fluid, which is then no longer net-electrically neutral, and responds to the field by moving.

A fluorescent dye YOYO-1 is used in the solution. It is so named for its conformation, which is an ethidium homodimer. This is an intercalating dye, which means that it binds to the entire length of the DNA molecule by inserting itself into the base-stacking zone of the DNA chain. The dye has a nice property that the fluorescence is greatly enhanced (10,000×) when the molecule is conjugated with DNA, so minimal background fluorescence from unbound dye free in solution is produced. For that matter, there is very little dye left in solution, because the binding is extremely tight between the dye and the DNA molecule. YOYO-1 excites near 490 nm wavelength, and emits near 514 nm. The insertion of these dyes tends to increase the contour length of the molecule. A dye-to-base-pair ratio of 1:10 is used in one embodiment.

The DNA is stained by first preparing a mixture of YOYO-1 dye and the 5×TBE buffer solution and about 3\% vol/vol. of β-mercaptoethanol. The latter is a reducing agent which scavenges oxygen radicals from the solution, thereby reducing the rate of photobleaching of the dye. The dye, 5×TBE and the β-mercaptoethanol are mixed together and then the DNA is added afterwards. A good value of concentration for working with nanofluidic devices seems to be in the range of 10 uM DNA base-pairs. To achieve the 1:10 dye-to-base-pair ratio for this concentration of DNA, 1 uM YOYO-1 is used. The DNA is allowed to sit for 1 hour at room temperature, and then incubated at 40° C. for 10 minutes. The DNA solution is then ready to be loaded into the devices.

Reservoirs 430 and 435 for fluid and electrodes are attached to the front face of barrier 415 using silicone RTV elastomer. The resevoirs are cylindrical sections of polypropylene tubing about 2.5 mm in length. This length allows a microscope objective to clear the reservoirs and still focus on the surface. A small hole about ½ mm is drilled in the side of each reservoir, and a platinum electrode 440, 445 is inserted through the hole into the interior of each reservoir.

The sample to be analyzed is injected into one of the reservoirs, and a glass cover 430, 435 approximately 0.1 mm thick and 4 mm×4 mm square is smeared with vacuum grease and fastened to the top of the reservoir to prevent evaporation. The liquid fills the devices by capillary action, so no special measures are required except to wait approximately 10 minutes before filling the reservoir at the opposite to prevent trapping of bubbles in the center of the device.

Occasionally bubbles may be trapped in inconvenient places, and in these cases, the bubbles are removed by a combination of electric fields and alternating warm and cool ambient temperatures. Degassing is a procedure for removing dissolved gas by putting the liquids in a chamber at under vacuum. Use of degassing small volumes of liquid can speed re-absorption of trapped gas.

Typical runs use a pulse duration varying from 0.1 seconds up to 8 seconds. The recoil time allowed is increased as a multiple of the drive duration. Though according to theory, the recoil time is expected to go as the square of the drive duration, the program of recoil durations used is always above the required duration to minimize impact on the data.

Figure 5:
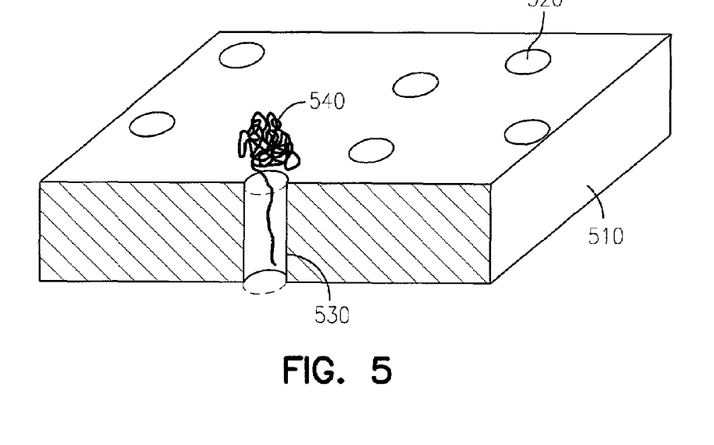
FIG. 5 is a perspective view of a porous membrane used to create a force barrier.

In FIG. 5, an alternative free energy barrier is a membrane 510 shown in perspective with a portion in cross section. The membrane has a plurality of pores 520, one of which is shown in cross section at 530 with a molecule 540 shown partially into pore 530. In some embodiments, the pore size varies between 15 nm and 1 um. For smaller pores, the thickness of the membrane is approximately 6 um, and may be thicker for larger pore size, such as a thickness of between approximately 20-30 um. Smaller size pores may also work, but perhaps not quite as well The density of the pores may be varied as desired given structural integrity limitations of the membrane.

Such membranes are commercially available and are manufactured by techniques such as the track-etch technique known in the art of membrane filter manufacture. In this technique, a polycarbonate membrane is subjected to bombardment by high-energy ionic nuclear fragments. These fragments cause chemical changes to the polymer matrix in the vicinity of the path along which the ion travels. These chemical changes change the solubility of the matrix in some etchants, such as potassium hydroxide, allowing the tracks to be developed into small holes. These holes can be made very regular in size and shape, and can range in size from 10 nm in diameter or smaller up to several microns. In the present embodiment, the membrane is contacted with the medium in which the molecules are suspended and the force on the molecules is directed perpendicular to the membrane. The free-energy barrier is formed by the lower entropy of molecules situated inside the pores in the membrane. A further embodiment is several of these membranes stacked together to form an array of juxtaposed barriers in which separation occurs. This embodiment involves some contrivance to prevent the membranes from becoming stuck together. This can be an open fabric of fine threads separating adjacent membranes, or it can comprise surface texure modification of the membrane itself to restrict contact between adjacent membranes to those areas elevated by the texturing.

Figure 6:
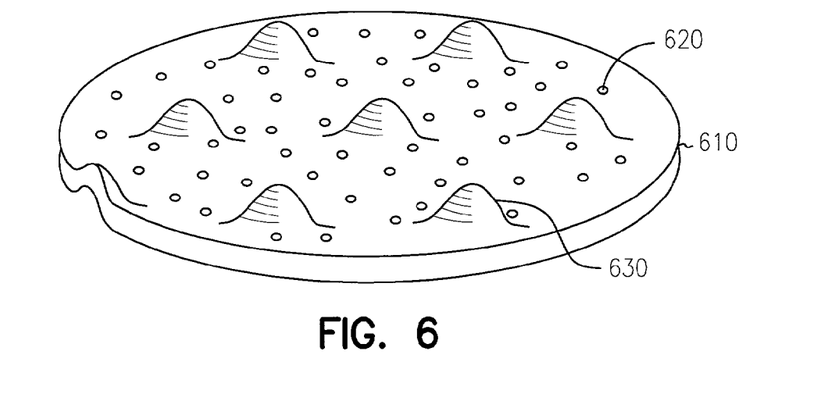
FIG. 6 is a perspective view of a porous membrane having additional surface features.

A further embodiment of a membrane 610 serving as a free energy barrier is shown in FIG. 6. In this embodiment, the membrane has similar parameters as membrane 510, but in addition to pores 620, also has a plurality of surface features, such as bumps 630 to prevent contact between adjacent structures, such as further membranes. In one embodiment, the surface features are formed when the membrane is cast. A surface on which a film for the membrane is cast, contains dimples corresponding to the surface features. In further embodiments, the features may be ridges or other structures providing the ability to separate the membrane from other structures. An alternative technique for making the membrane film comprise embossing using well known techniques commonly used in the manufacture of compact discs.

Bumps 630 are spaced approximately 2 um apart in one embodiment, with a height approximately 1 um tall. In further embodiments, the bumps 630 are approximately 5-6 um tall, and approximately 20-30 um apart. In still further embodiments, both sides of the membrane contain bumps.

Figure 7:
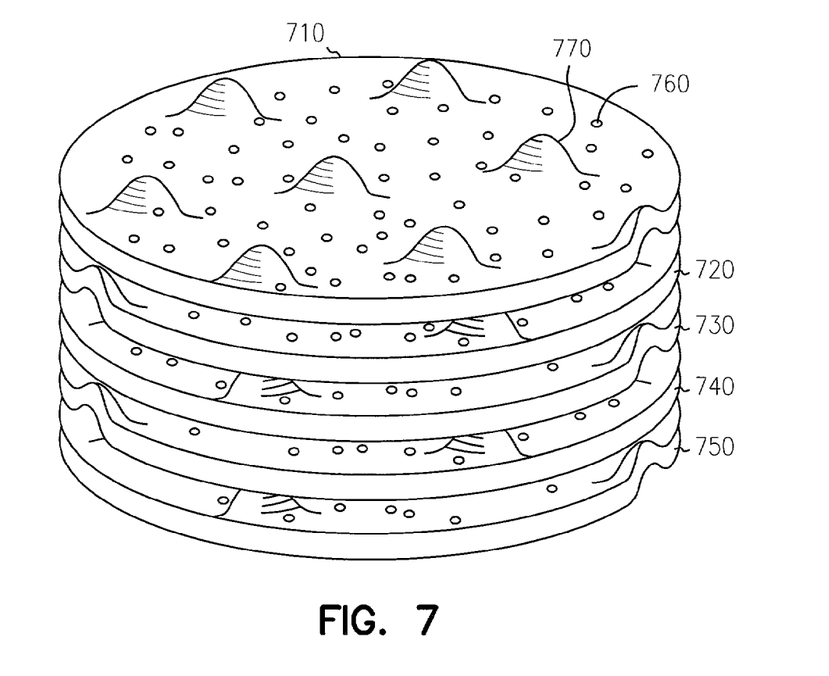
FIG. 7 is a perspective view of a plurality of juxtaposed porous membranes having addition surface features.

FIG. 7 illustrates a plurality of juxtaposed adjacent membranes 710, 720, 730, 740 and 750. Each membrane has a plurality of pores 760 and bumps 760. The membranes are spaced at least approximately twice the diameter of the pores to ensure acceptable entropic confinement. If too close, there is no entropic barrier. If further apart, more time is required for molecule drift to move molecules through the membranes.

In one embodiment of the invention, successive membranes are rotated when assembled to ensure that bumps do not mate, and reduce the distance between adjacent membranes. In further embodiments, at least two different patterns of bumps are available for alternating membranes to ensure proper distance. In yet further embodiments, no bumps are required, and the membranes are held in place by suitable frames positioned between reservoirs. Such membranes are thick enough, and separated far enough to ensure flexing of membranes does not bring them too close together.

In the normal operation of the method of this invention, the longest length of molecule that can be effectively separated is related to the longitudinal dimension of the high free-energy region of the device. For example, if the membrane embodiment is considered, and the membrane has a thickness of 20 microns, the longest strand of DNA that could be effectively separated will be some multiple of 20 microns, depending on the degree of elongation of the molecule as it passes through the high-free energy region. Typical values of this multiple will be between 1 (in the limit of extreme elongation) to 5 (for weakly elongated molecules). This provides a performance limitation in cases where the longitudinal dimension of the high-free energy region is limited.

Figure 8:
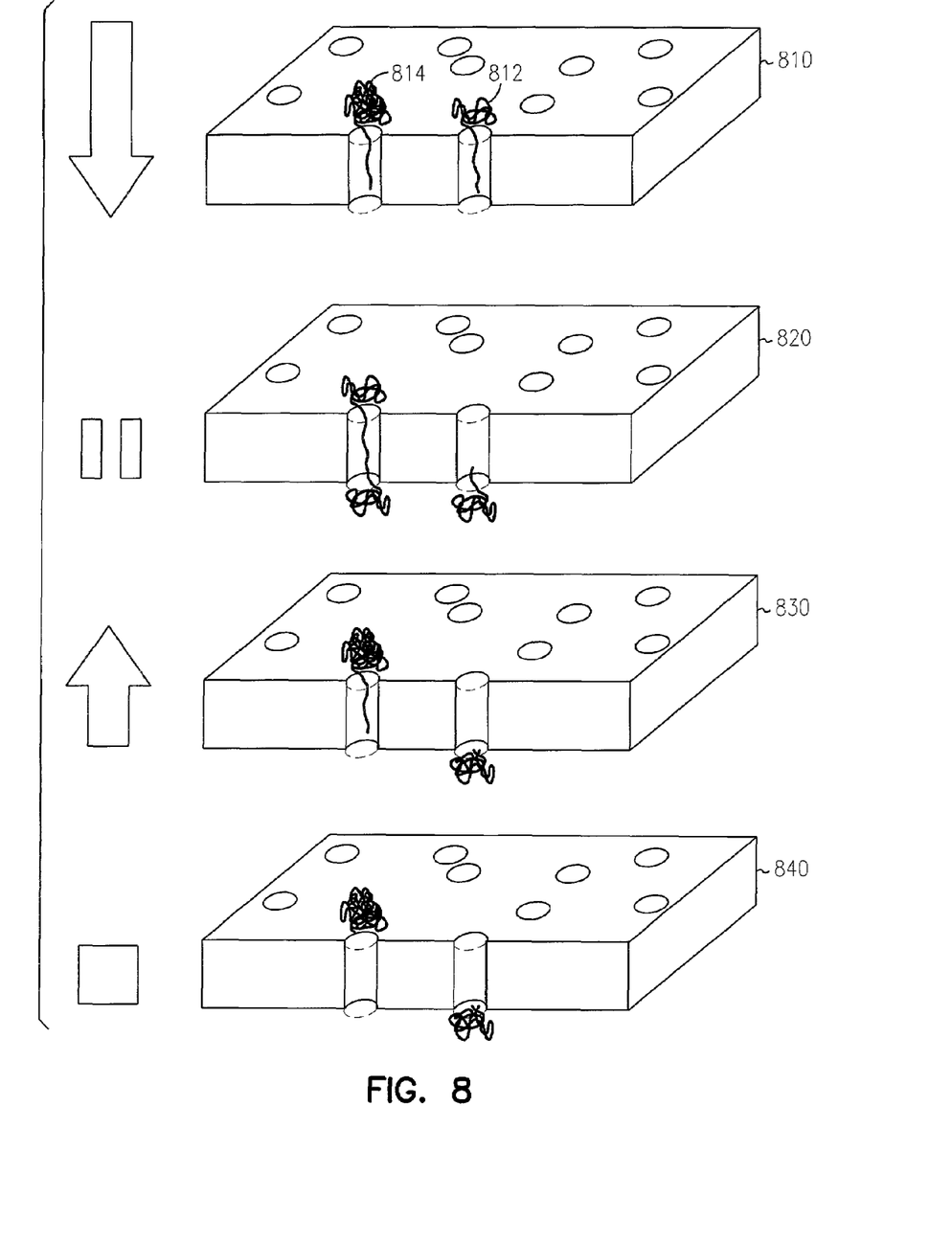
FIG. 8 is a time sequence illustrating molecule movement through different phases of application of force.

FIG. 8 provides a time sequence illustration of an alternative electric field pulsing algorithm using a membrane 10 microns in thickness, and a DNA molecule 50 microns in length. An electric field is applied at 810, causing both a short molecule 812 and a long molecule 814 to enter respective pores. In this system, the leading end of the molecule would emerge from the downstream side of the high free-energy region before the trailing end of the molecule would clear the low free-energy region on the upstream side, as is required to discriminate lengths.

When the field is removed, the molecule enters a metastable state—i.e. the total free energy is elevated by the occupancy of the molecule in the high free-energy region but there is no impetus to recoil because a small change in position of the molecule does not change the energy of the molecule. This state is illustrated at 820. In this configuration, movement causes DNA to be drawn from one of the low-energy regions in order to deliver it to the other for which there is no net change in energy.

One method for overcoming this limitation is to apply a drive pulse as described herein and allow the molecules to pass through the meta-stable state as described above. In this case, for a given pulse duration, a long molecule might remain in the metastable state at the end of the pulse, while a shorter molecule will have passed through the metastable state, and accumulated entirely on the downstream side of the high free-energy region as indicated at 820. Now, the longer molecule will not recoil on its own, so a pulse of retrograde force is applied below the critical force required to initiate passage into the high free-energy region as illustrated at 830. The shorter molecule completely on the downstream side of the high free-energy region remains in that region for lack of sufficient force to insert it into the high free-energy region. The longer molecule straddling the high free-energy region will move readily because no energy change is required for its motion. This state is illustrated at 840. The retrograde pulse must be sufficiently long to completely recoil all molecules in the metastable state to the upstream side of the high free-energy region. In this manner the same conceptual mechanism can be applied in the absence of a long high free-energy region. This method has an additional advantage that the adverse scaling of recoil time with molecule length is eliminated. In this case the recoil time scales linearly with the molecule length. As before the process can be repeated with the same or different pulse programs to continue to separate in the same region of lengths or different regions of length. Also as before, many barriers can be presented sequentially to enhance the resolution of the technique.

CONCLUSION

Separation of long molecules by length is obtained by forcing such molecules to traverse a boundary between a low free-energy region and a high free-energy region. In one embodiment, the high free-energy region is a dense pillar region or other structure formed on a semiconductor substrate. The low free-energy region is a larger chamber or structure formed adjacent the high free-energy region. Other structures and force barriers may also be used as is apparent from the description. Further, while an electric field is pulsed to provide the force on the molecules, other forces may also be used consistent with the force barrier, such as gravity, pressure and centrifugal force.

Structures for practicing the invention were also described. It should be noted that the specifications thereof were highly dependent on the size of the molecules, and that they will change for different sized molecules. Further, the specification may also be changed for operation on the same sized molecules as described above to while still obtaining benefits provided by the invention.

The invention claimed is:

1. A method of separating molecules of varying length, the method comprising:
   (a) providing an apparatus that comprises a chamber having a first region that is adjacent to a second region, wherein the first region comprises a lower free-energy than the second region, and wherein the second region comprises a plurality of nanospaced pillars, and a composition comprising molecules of varying lengths in a fluid disposed in said first region;
   (b) applying a predetermined driving force appropriate to drive specific length molecules from the first region entirely into the second region, and to drive molecules longer than the specific length from the first region partially into the second region;
   (c) reducing or removing the driving force to cause molecules that are longer than the specific length molecules and that are not driven entirely into the second region during the application of the driving force to recoil back into the first region, thus resulting in the separation of molecules based on length, wherein the first region comprises a sufficiently lower free-energy than the second region such that the step of reducing or removing the driving force alone effects the recoil.

2. The method of claim 1, wherein the driving force is applied for a predetermined duration.

3. The method of claim 1, wherein prior to applying the driving force, the method further comprises applying a predetermined gathering force that is less than the driving force.

4. The method of claim 1, further comprising applying a retrograde force after reducing or removing the driving force to facilitate recoiling the molecules longer than the specific length molecules into the first region.

5. A method of separating molecules of varying length, the method comprising:
   (a) providing an apparatus that comprises a chamber having a first region that is adjacent to a second region, wherein the second region comprises a plurality of nanospaced pillars and the first region has a higher entropy relative to the second region;
   (b) placing a composition comprising molecules of varying lengths in a fluid in the first region;
   (c) forcing the molecules to a boundary between the first region and the second region;

(d) applying a field pulse to drive molecules into the second region, wherein some molecules of the composition are driven entirely into the plurality of nanospaced pillars of the second region while the remaining molecules of the composition are longer compared to said molecules driven into the second region, and said remaining molecules are not driven entirely into the second region;

(e) reducing or removing the field pulse;

(f) allowing one or more molecules that are not driven entirely into the second region to recoil into the first region, thus separating molecules based on length; and (g) repeating the steps of (c) through (f) to effect separation of a range of lengths that would otherwise not be separated without the repeating step.

6. The method of claim 5, wherein a predetermined subcritical field is used to force molecules to the boundary.

7. The method of claim 5, wherein the field pulse is a predetermined value appropriate to drive specific length molecules entirely into the second region.

8. The method of claim 5, wherein the field pulse is applied for a predetermined duration.

9. The method of claim 7, further comprising applying a retrograde force after reducing or removing the field pulse to facilitate recoiling the molecules longer than the specific length molecules into the first region.

10. The method of claim 5, wherein the steps of (b) through (e) are repeated with varying predetermined duration and/or field strength.

11. The method of claim 9, wherein the retrograde force is applied in a lateral direction relative to a direction of travel of the molecules between regions.

12. A method of separating molecules of varying length, the method comprising:

(a) providing an apparatus that comprises a chamber having a first region that is adjacent to a second region, and a composition comprising molecules of varying lengths in a fluid disposed in said first region;

(b) applying a driving force appropriate to drive specific length molecules from the first region entirely into the second region, wherein the first region is of lower free-energy than the second region and the second region comprises a plurality of nanospaced pillars; wherein molecules longer than the specific length are partially driven into the second region;

(c) applying a retrograde force to facilitate recoiling the molecules longer than the specific length molecules partially within the second region back into the first region after reduction or removal of the driving force, thus resulting in the separation of molecules based on a specific length, wherein the retrograde force is applied in a lateral direction relative to a direction of travel of the molecules between regions; and (d) repeating the steps of (b) through (c) to effect separation of a range of lengths that would otherwise not be separated without the repeating step.

13. The method of claim 12, wherein the retrograde force is less than the driving force.

14. A method of separating molecules of varying length, the method comprising the steps of:

providing an apparatus that comprises a chamber having a first region that is adjacent to a second region that comprises a plurality of nanospaced pillars;

placing a composition comprising molecules of varying lengths in a fluid disposed in said first region, wherein the molecules comprise a first group of molecules having a first length and a second group of molecules having a second length longer than the first length;

applying a driving force to drive molecules from the first region into a second region, wherein the first region comprises a lower free-energy than the second region, wherein the molecules of the first group are driven entirely into the second region while the molecules of the second group are only partially driven into the second region, and applying a retrograde force in a lateral direction relative to a direction of travel of the molecules between the regions to recoil molecules only partially driven into the second region back into the first region, thus resulting in the separation of molecules based on length.

15. The method according to claim 14, wherein the driving force is of a predetermined strength appropriate to drive the first group of molecules entirely into the second region and drive the second group of molecules partially into the second region.

16. The method according to claim 14, wherein the driving force is applied for a predetermined duration.

17. The method according to claim 14, wherein prior to applying the driving force, the method further comprises applying a predetermined gathering force that is less than the driving force to move the molecules to a barrier between the first region and the second region.

18. The method of claim 14, wherein the retrograde force is applied after reducing or removal of the driving force.

* * * * *